(12) United States Patent
Lenke et al.

(10) Patent No.: US 6,830,571 B2
(45) Date of Patent: Dec. 14, 2004

(54) CONTOURABLE SPINAL STAPLE WITH CENTRALIZED AND UNILATERAL PRONGS

(75) Inventors: Lawrence G. Lenke, St. Louis, MO (US); Joseph W. Tai, Bartlett, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/356,988

(22) Filed: Feb. 3, 2003

(65) Prior Publication Data

US 2003/0120275 A1 Jun. 26, 2003

Related U.S. Application Data

(63) Continuation of application No. 09/628,761, filed on Jul. 31, 2000, now Pat. No. 6,533,787.

(51) Int. Cl.[7] ............................................. A61B 17/56
(52) U.S. Cl. ........................................ 606/61; 606/75
(58) Field of Search ............................ 606/61, 69, 70, 606/71, 75, 151; D24/145, 140

(56) References Cited

U.S. PATENT DOCUMENTS

| | | | |
|---|---|---|---|
| 4,047,524 A | | 9/1977 | Hall |
| D274,095 S | * | 5/1984 | Kenna ........................ D24/140 |
| 4,651,724 A | | 3/1987 | Berentey et al. |
| 4,960,420 A | * | 10/1990 | Goble et al. ................... 606/72 |
| 5,108,395 A | | 4/1992 | Laurain |
| 5,147,361 A | | 9/1992 | Ojima et al. |
| 5,306,275 A | | 4/1994 | Bryan |
| 5,314,427 A | * | 5/1994 | Goble et al. ................... 606/72 |
| 5,487,741 A | | 1/1996 | Maruyama et al. |
| 5,603,714 A | | 2/1997 | Kaneda et al. |
| 5,616,144 A | | 4/1997 | Yapp et al. |
| 5,620,443 A | | 4/1997 | Gertzbein et al. |
| 5,899,904 A | | 5/1999 | Errico et al. |

FOREIGN PATENT DOCUMENTS

| | | |
|---|---|---|
| DE | 9217768 | 8/1993 |
| EP | 0615728 | 9/1994 |
| EP | 0820730 | 7/1997 |

OTHER PUBLICATIONS

*Anterior Spinal Fixation After Lumbar Corpectomy*, by Thomas Zdeblick, M.D., Osamu Shirado, M.D., Paul C. McAfee, M.D., Henry DeGroot, M.D. & Karen E. Warden, © 1991 by the *Journal of Bone and Joint surgery, Incorporated*.

*Kaneda Anterior Spinal Instrumentation System* and *Kaneda Anterior Spinal Screws*, by AcroMed Corporation, p. B–12.

*Kaneda Anterior Spinal Instrumentation for the Thoracic and Lumbar Spine*, by Kiyoshi Kaneda, pp. 413–422.

\* cited by examiner

*Primary Examiner*—Todd E. Manahan
(74) *Attorney, Agent, or Firm*—Woodard, Emhardt, Moriarty, McNett & Henry LLP

(57) ABSTRACT

A staple for stabilizing the attachment of a vertebral screw and a longitudinal member to the spine. The staple has a plate with first and second apertures. All the staple's legs, prongs, or spikes attached to the underside of the staple are located closer to one particular aperture than the other. Preferably, the plate is also "bow-tie" shaped with a groove that separates the wings of the bow-tie. This bow-tie or hour glass shape combined with the groove help the surgeon to more easily conform the plate to the patient's vertebra.

20 Claims, 5 Drawing Sheets

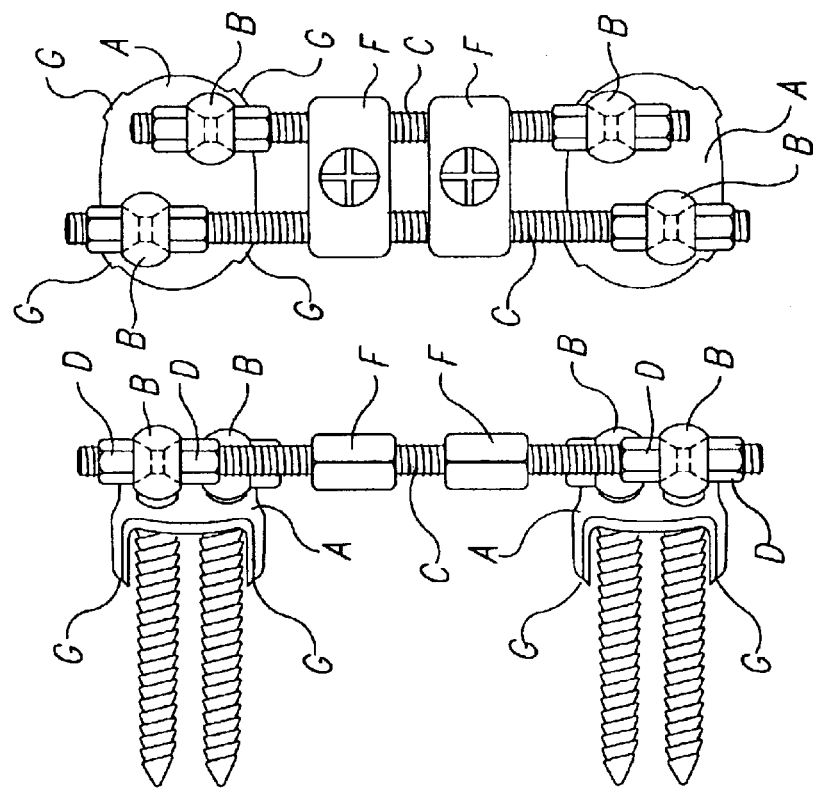
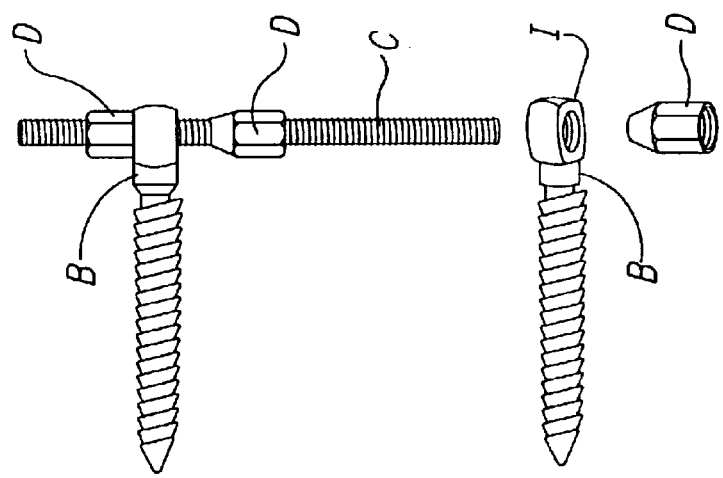
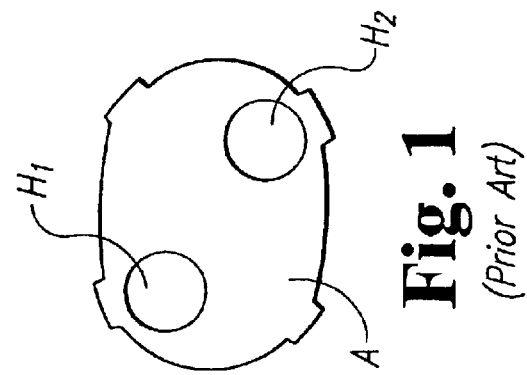

CONTOURABLE SPINAL STAPLE WITH CENTRALIZED AND UNILATERAL PRONGS

REFERENCE TO RELATED APPLICATIONS

This application is a continuation application of U.S. patent application Ser. No. 09/628,761 filed on Jul. 31, 2000, now U.S. Pat. No. 6,533,787 the contents of which are hereby incorporated by reference.

BACKGROUND OF THE INVENTION

This invention relates to surgical spinal implant systems, and particularly to those using spinal rods contoured for connection at various locations along the spinal column.

Spinal fractures often occur at the thoracolumbar junction. Most of these fractures are burst injuries, which are particularly dangerous because retropulsed bone fragments can cause spinal cord or caudal equina injuries. Posterior fixation has long been the primary approach for traumatic spinal injuries of this type.

The development of posterior internal fixation procedures for burst fractures was a substantial improvement over early approaches of bed rest and body casts. Several disadvantages to posterior fixation were, however, discovered. For example, this approach fails to reduce kyphosis or allow complete clearing of the spinal canal. Other complications include psuedoarthroses, late rod disengagement and inadequate reduction. Some posterior instrumentations require the fusions to extend at least two levels above and below the injury, particularly at the thoracolumbar junction. The posterior approach is also limited in the viability for use in burst fractures because in such fractures, neural compression generally occurs from the anterior direction. Therefore, it is generally better to decompress and fuse the spine from the anterior.

There are several advantages to anterior internal fixation. An anterior approach allows complete clearance from the spinal canal of bone fragments and for total resection of a tumor. It also permits fusion of a minimal number of motion segments. Yet in spite of these advantages, the use of anterior approaches has been limited by the risk of complications or other disadvantages.

Several plate and screw systems have been designed for anterior instrumentation of the spinal column. The Syracuse I-Plate may use rigid or semi-rigid screws in combination with a plate. But distraction or compression of the bone graft is not possible with this system. The CASF Plate marketed by AcroMed is designed to be used in a semi-rigid manner. This device, as well, does not permit compression or distraction of the bone graft and in addition cannot be used in a rigid construct. The Stafix Plating System marketed by Daruma of Taipei, Taiwan is an anterior thoracolumbar plate designed to address similar indications. This plate incorporates slots and holes as well as permitting quadrilateral placement of screws. The Anterior Thoracolumbar Plating System (Medtronic Sofamor Danek) is a slotted plate designed to attach to the anterior lateral aspect of the vertebral body. The plate allows distract and/or compression through the use of two screws and two bolts.

Several modular spinal instrumentation systems have also been developed for anterior procedures. One such device, the Kaneda device, is shown in FIGS. 1 to 6. As shown, the device extends fixation one vertebral level cephalad and one level caudal to the vertebra in question. A typical construct has two vertebral body staples A, four vertebral screws B, two rods C, eight nuts (one on each side of a screw) and two transverse fixators F. Each vertebral body staple A has four spikes, one on each corner of the staple, to initially secure the staple to a vertebra. Vertebral screws B are then placed through holes H1 and H2 into the cephalad and caudal vertebrae. Rods C are located in the holes I in each screw B with the internal nuts D loosely threaded on each rod. The external nuts, also identified as "D" are then threaded onto the rods. Thereafter, the surgeon tightens all nuts against each side of a screw with the surgeon applying compressive or distractive forces as required. The anterior and posterior rods C are then coupled with transverse fixators F. Specific indications for such modular devices may include deficient anterior bone mass due to trauma, tumor, infection, degenerative disease, congenital causes, or deformity.

The Kaneda system is not entirely satisfactory, largely resulting from the design of vertebral staple A. The staple is used to stabilize screw B much the same way as a washer is used to stabilize a bolt in most any mechanical attachment. These staples, however, are placed on a vertebra, not a uniformly flat surface. Hence, the staple curvature should ideally match the contour of the surface of the vertebra before use. And even if the fit is perfect, it may still be unsatisfactory if the spikes on one end, say the two near hole H1, are pulled from the vertebra when a screw is tightened in the hole on the other end, H2 in our example. This "rocking" effect is depicted in FIG. 7.

Further details regarding staples in a spinal fixation device can be found in Kiyoshi Kaneda, *Kaneda Anterior Spinal Instrumentation for the Thoracic and Lumbar Spine*, Spinal Instrumentation, Williams & Wikins, (Baltimore, Hong Kong, London, Munich, Philadelphia, Sydney, Tokyo), pp. 413 et seq, the disclosure of which is specifically incorporated into this specification by reference.

As a result, there is a need for a vertebral staple in a modular system that can be more easily contoured to the surface of a vertebra, and that does lift spikes on one side of the staple from the vertebra when the other side is tightened. The following is one solution to this need.

SUMMARY OF THE INVENTION

In one aspect, this invention is a vertebral staple with a plate having at least two apertures to receive a spinal bolt, and at least two legs (also identifiable as prongs or spikes) integrally mounted to the bottom of the plate and wherein all legs mounted on the bottom of the plate are closer to one particular aperture for passing a spinal bolt than another aperture for passing a spinal bolt.

In another aspect, this invention is a vertebral staple with a plate having at least two apertures to receive a spinal bolt. The bottom of the plate has at least one leg (also identifiable as a prong or a spike) integrally mounted near the lateral edge of the plate, and at least one leg integrally mounted on the interior of the plate, with all legs mounted on the bottom of the plate closer to one particular aperture for passing a spinal bolt than another aperture for passing a spinal bolt.

In yet another aspect, this invention is a vertebral staple with a plate having a groove therein dividing the plate into a first portion and a second portion. Each of the first and second portions have at least one aperture for passing a bone bolt through the plate and into the vertebra to which the staple is attached. In addition, the bottom of the first portion of the plate has at least two legs (also identifiable as prongs or spikes) integrally attached to the plate, while no legs are mounted on the bottom of the second portion of the plate.

BRIEF DESCRIPTION OF THE DRAWINGS

FIG. 1 is a plan view of a prior art vertebral staple.

FIG. 2 is an exploded view of a prior bone bolt and longitudinal member.

FIGS. 3 and 4 are respectively side and plan views of a prior art spinal fixation system.

DESCRIPTION OF THE PREFERRED EMBODIMENTS

Figure 6:
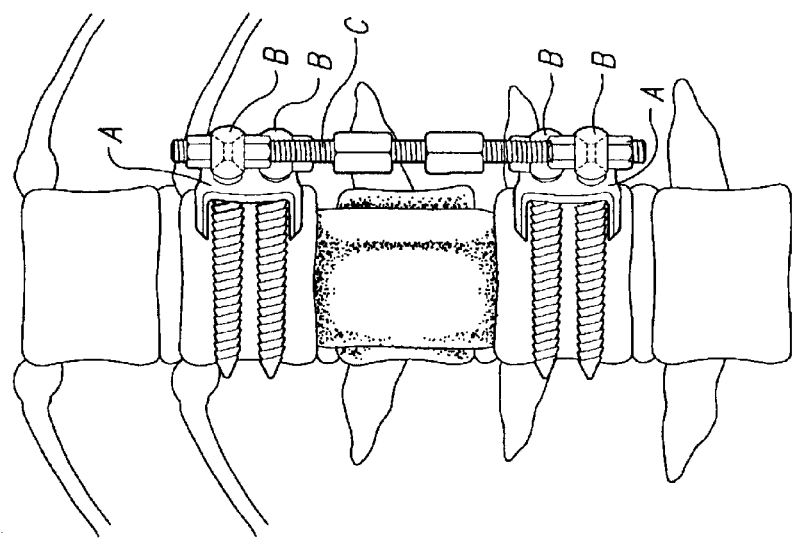
FIGS. 5 and 6 are respectively plan and side views of a prior art spinal fixation system shown attached to the spine.
Figure 5:
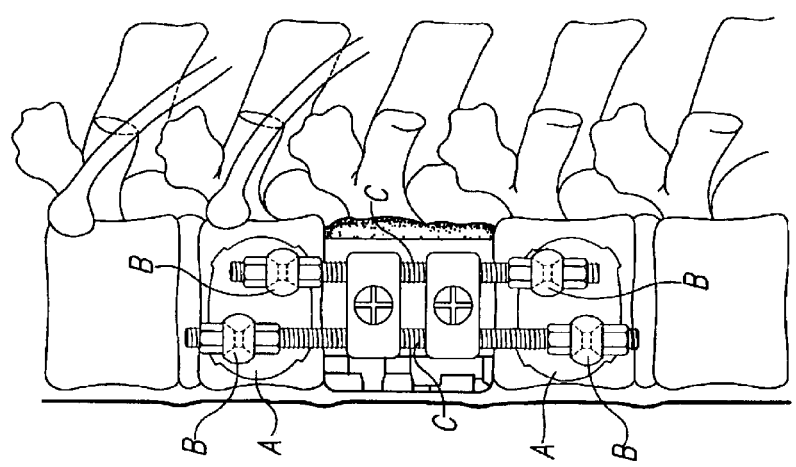
Figure 7:
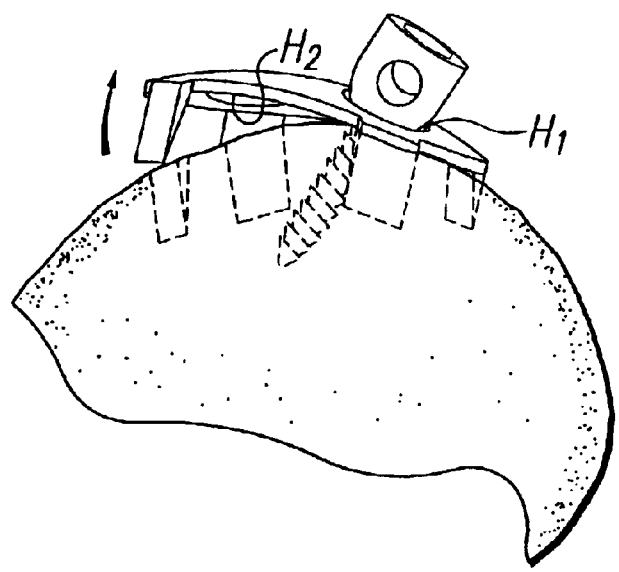
FIG. 7 is a side view of a prior art vertebral staple.

For the purpose of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the illustrated invention being contemplated as would normally occur to one skilled in this art.

Figure 8:
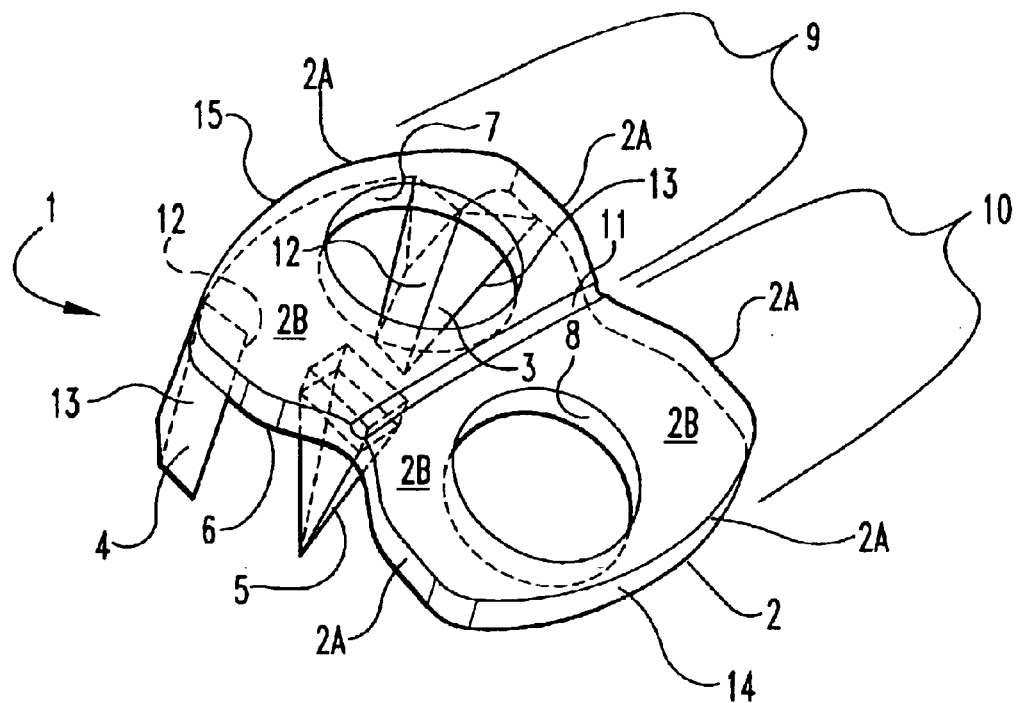
FIG. 8 is a perspective view of one embodiment of the present invention.

A spinal staple 1 according to the preferred embodiment of the present invention is depicted in FIG. 8. Staple 1 has a preferably bow-tie shaped body 2. The body 2 has a lateral edge 2A and an interior 2B. Body 2 can generally be subdivided in two halves by a groove 11. The first half 9 or wing 9 contains a hole 7 and the second half 10 or wing 10 contains a hole 8. Holes 7 and 8 can be either threaded or unthreaded and, as illustrated in FIG. 8, are preferably substantially the same size and shape. Additionally, the holes or apertures 7 and 8 are arranged cater-cornered to one another relative to the staple body 2, as illustrated in FIGS. 8 and 9, so as to be offset from one another in both a lateral direction (i.e., in a direction extending alone the first and second halves 9, 10) and an axial direction (i.e., in a direction extending alone the groove 11).

Three legs 3–5, prongs 3–5, or spikes 3–5 are attached to body 2 on the underside 6 of the first half 9. Legs 3 and 4 are unilateral with respect to body 2. Meaning, legs 3 and 4 are commonly attached near one end of the staple so that both legs 3 and 4 are more closely adjacent legged hole 7 than non-legged hole 8. Situated in this manner, legs 7 and 8 preferably attach toward the posterior side of the patient's vertebra, depending on the surgeon's installation. The third leg 5 is centrally mounted in the interior of body 2, preferably closer to legged hole 7 than non-legged hole 8, preferably on the same side of groove 11 as legs 3 and 4, and preferably not under groove 11.

Figure 9:
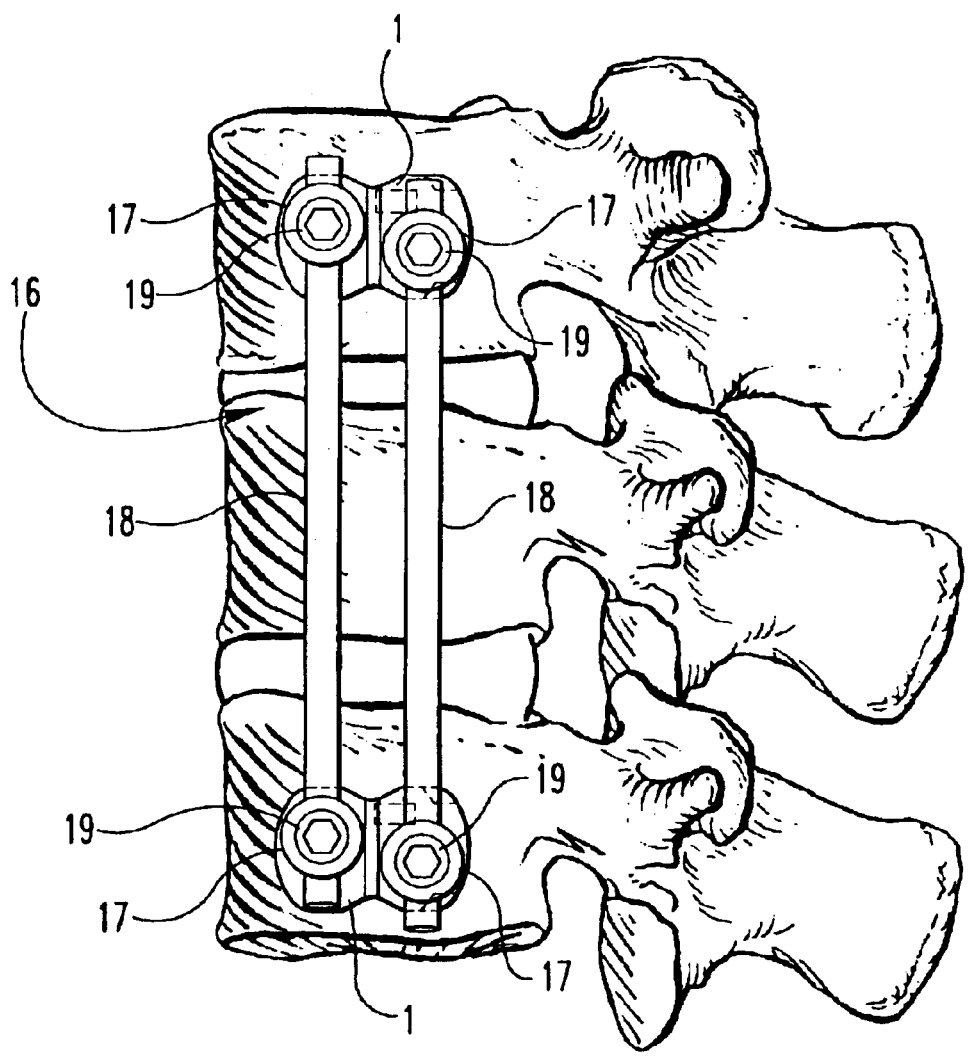
FIGS. 9, 10, and 11 are respectively front, top, and side views of spinal fixation systems that incorporate one embodiment of the present invention.

As illustrated in FIGS. 8 and 9. the interior or inner leg or prong 5 overlaps a portion of the aperture 7 in the axial direction (along the groove 11), and also overlaps a portion of the aperture 8 in the lateral direction (along the first and second halves 9, 10). As also illustrated in FIGS. 8 and 9, each of the outer legs or prongs 3, 4 is offset from the inner leg prong 5 in both the axial direction and the lateral direction. Additionally, the outer legs or prongs 3, 4 also overlap a portion of the aperture 7 in the axial direction. In the illustrated embodiment, the inner prong 5 is positioned intermediate the outer prongs 3, 4 in the lateral direction.

The inside edge 12 of legs 3 and 4 is preferably perpendicular to the underside 6. The outside edge 13 then tapers inwardly of the staple to intersect inside edge 12. The shape of leg 5 can be most anything that will work. In one embodiment, it is pyramidal and extends the same distance from underside 6 as legs 3 and 4.

Body 2 is preferably slightly convex in shape when viewed axially along groove 11, ends 14 and 15 being slightly bent or curved toward each other, generally at groove 11. The bow-tie shape and/or the presence of groove 11 in the present invention allows the surgeon to more easily bend and to conform staple 1 to complement the surface of the spine. The "pinched" middle resulting from the bow-tie shape and the presence of groove 11 reduce the amount of metal that the surgeon must deform to conform the staple to the patient's vertebra if compared to prior art devices. The reduced metal also affords increased visualization of the anatomy directly under the staple.

Figure 10:
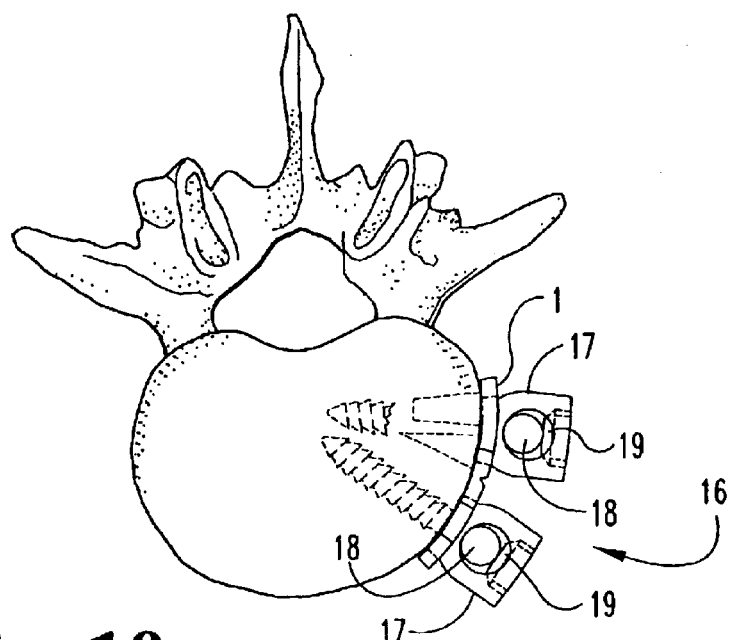
Figure 11:
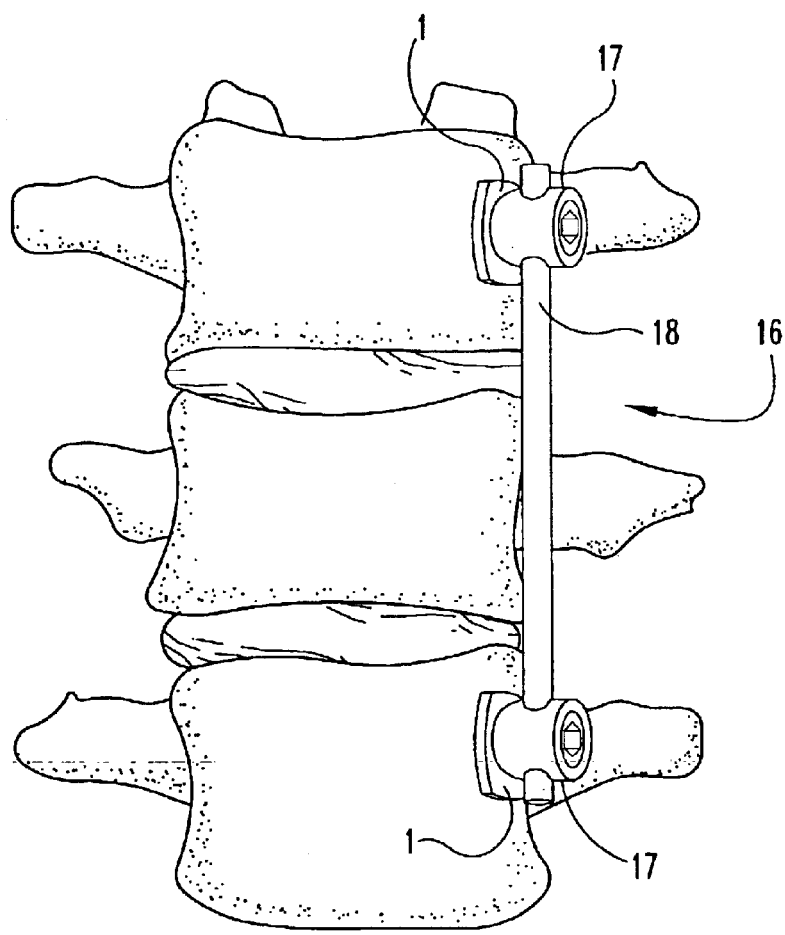

FIGS. 9–11 depict staple 1 in a spinal fixation system 16. System 16 has two vertebral staples, four vertebral bolts 17 or screws 17, two rods 18, and four clamps 19 or nuts 19 or plugs 19 to hold the rods 18 to screws 17. In this specification, the term "bolt" or "screw" refers to any various bone fasteners, including a standard bone screw, such as those sold under the trademark CD Horizon by Medtronic Sofamor Danek.

While the invention has been illustrated and described in detail and the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal staple fixation system, comprising:
   first and second staples adapted for engagement with respective first and second vertebral bodies, each of said first and second staples including:
   a plate defining an outer edge extending about an interior region, said interior region defining first and second apertures extending therethrough and arranged cater-cornered to one another such that said first aperture is offset from said second aperture in an axial direction and in a lateral direction; and
   a plurality of prongs extending from said plate, at least one of said prongs comprising an inner prong extending from said interior region of said plate, said inner prong overlapping a portion of said first aperture in said axial direction, said inner prong overlapping a portion of said second aperture in said lateral direction; and
   first and second rods extending between said first and second staples to interconnect the first and second vertebral bodies.

2. The spinal staple fixation system of claim 1, wherein another of said plurality of prongs extending from said plate is offset from said inner prong in said axial direction and in said lateral direction.

3. The spinal staple fixation system of claim 2, wherein said another of said plurality of prongs overlaps a portion of one of said first and second apertures in said axial direction.

4. The spinal staple fixation system of claim 1, wherein said inner prong is positioned closer to one of said first and second apertures than the other of said first and second apertures.

5. The spinal staple fixation system of claim 1, wherein each of said plurality of prongs are positioned closer to one of said first and second apertures than the other of said first and second apertures.

6. The spinal staple fixation system of claim 1, wherein said first and second apertures have a substantially identical size and shape.

7. The spinal staple fixation system of claim 1, wherein each of said first and second apertures are threaded.

8. The spinal staple fixation system of claim 1, wherein said inner prong has a rectangular-shaped base portion extending from said interior region of said plate and a pyramidal-shaped anchoring portion extending from said rectangular-shaped base portion.

9. The spinal staple fixation system of claim 1, further comprising a plurality of bone screws, each of said bone screws extending through a respective one of said first and second apertures in said plate, said first and second rods engaged with head portions of said plurality of bone screws.

10. A spinal staple, comprising:
a plate defining an outer edge extending about an interior region, said interior region defining first and second apertures extending therethrough and arranged cater-cornered to one another such that said first aperture is offset from said second aperture in an axial direction and in a lateral direction, said plate defining a lateral curvature corresponding to an outer profile of a vertebral body to which the spinal staple may be anchored; and
a plurality of prongs extending from said plate, at least one of said prongs comprising an inner prong extending from said interior region of said plate, said inner prong overlapping a portion of said first aperture in said axial direction, said inner prong overlapping a portion of said second aperture in said lateral direction.

11. The spinal staple fixation system of claim 10, wherein said inner prong has a rectangular-shaped base portion extending from said interior region of said plate and a pyramidal-shaped anchoring portion extending from said rectangular-shaped base portion.

12. A spinal staple fixation system, comprising:
first and second staples adapted for engagement with respective first and second vertebral bodies, each of said first and second staples including:
a plate defining an outer edge extending about an interior region, said interior region defining first and second apertures extending therethrough and arranged cater-cornered to one another such that said first aperture is offset from said second aperture in an axial direction and in a lateral direction; and
a plurality of prongs extending from said plate, at least one of said prongs comprising an inner prong extending from said interior region of said plate, said inner prong arranged closer to said first aperture than said second aperture in said axial direction, said inner prong arranged closer to said second aperture than said first aperture in said lateral direction; and
first and second rods extending between said first and second staples to interconnect the first and second vertebral bodies.

13. The spinal staple fixation system of claim 12, wherein said inner prong overlaps a portion of said first aperture in said axial direction and a portion of said second aperture in said lateral direction.

14. The spinal staple fixation system of claim 12, wherein another of said plurality of prongs extending from said plate is offset from said inner prong in said axial direction and in said lateral direction.

15. The spinal staple fixation system of claim 14, wherein said another of said plurality of prongs overlaps a portion of one of said first and second apertures in said axial direction.

16. The spinal staple fixation system of claim 12, wherein said first and second apertures have a substantially identical size and shape.

17. The spinal staple fixation system of claim 12, wherein said inner prong has a rectangular-shaped base portion extending from said interior region of said plate and a pyramidal-shaped anchoring portion extending from said rectangular-shaped base portion.

18. The spinal staple fixation system of claim 12, further comprising a plurality of bone screws, each of said bone screws extending through a respective one of said first and second apertures in said plate, said first and second rods engaged with head portions of said plurality of bone screws.

19. A spinal staple, comprising:
a plate defining an outer edge extending about an interior region, said interior region defining first and second apertures extending therethrough and arranged cater-cornered to one another such that said first aperture is offset from said second aperture in an axial direction and in a lateral direction, said plate defining a lateral curvature corresponding to an outer profile of a vertebral body to which the staple may be anchored; and
a plurality of prongs extending from said plate, at least one of said prongs comprising an inner prong extending from said interior region of said plate, said inner prong arranged closer to said first aperture than said second aperture in said axial direction, said inner prong arranged closer to said second aperture than said first aperture in said lateral direction.

20. The spinal staple fixation system of claim 19, wherein said inner prong has a rectangular-shaped base portion extending from said interior region of said plate and a pyramidal-shaped anchoring portion extending from said rectangular-shaped base portion.

* * * * *